United States Patent [19]

Eby, III

[11] Patent Number: 5,286,748

[45] Date of Patent: Feb. 15, 1994

[54] GENERAL METHOD OF SHORTENING THE DURATION OF COMMON COLDS BY APPLICATION OF MEDICAMENTS TO TISSUES OF ORAL CAVITY

[76] Inventor: George A. Eby, III, 2109 Paramount Ave., Austin, Tex. 78704

[21] Appl. No.: 799,607

[22] Filed: Nov. 27, 1991

Related U.S. Application Data

[63] Continuation-in-part of Ser. No. 633,043, Dec. 24, 1990, Pat. No. 5,095,035, which is a continuation-in-part of Ser. No. 182,983, Apr. 18, 1988, Pat. No. 5,002,970, and a continuation-in-part of Ser. No. 102,750, Sep. 24, 1987, Pat. No. 4,956,385, which is a continuation of Ser. No. 667,097, Nov. 1, 1984, abandoned, which is a continuation-in-part of Ser. No. 378,479, May 14, 1982, Pat. No. 4,503,070, which is a continuation-in-part of Ser. No. 288,750, Jul. 31, 1981, abandoned, which is a continuation-in-part of Ser. No. 22,620, Jan. 5, 1981, abandoned.

[51] Int. Cl.$^5$ .............. A61K 9/20; A61K 31/315; A01N 55/02
[52] U.S. Cl. .................... 514/494; 424/435; 424/440; 424/464; 424/468; 514/964; 514/965; 514/948; 514/974
[58] Field of Search ............. 514/974, 964, 965, 948, 514/494, 888, 889; 424/435, 440, 464, 468

[56] References Cited

U.S. PATENT DOCUMENTS

Re. 33,465  11/1990  Eby ....................... 424/464
2,540,253   2/1951   Gakenheimer ............. 514/772.7

(List continued on next page.)

FOREIGN PATENT DOCUMENTS

43616     1/1982  European Pat. Off.
59-31679  2/1984  Japan.

OTHER PUBLICATIONS

"Reduction in Duration of Common Colds by Zinc Gluconate Lozenges in a Double-Blind Study", G. A. Eby et al., 1984, Antimicrob. Agents Chemother.
"Prophylaxis & Treatment of Rhinovirus Colds with Zinc Gluconate Lozenges", W. Al-Nakib et al., 1987, J. of Antimicrob. Chemother.
"Zinc Gluconate & The Common Cold: A Controlled Clinical Study", J. C. Godfrey et al., 1992, J. International Medical Research.
"Cotton Bract Tannin: A Novel Human T-Lymphocyte Mitogen and a Possible Causative Agent of Byssinosis", Vuk-Pavlovic, Int. Arch. Appl. Immunol., 1988.
"Induction of Interleukin-1-Beta Release from Human Monocytes by Cotton Bract Tannin", Vuk-Pavlovic et al., 1990, Int. Arch Allergy Immunol.
"Distribution and Removal of Human Serum Albumin-Technetium 99m Instilled Intranasally", 1976, Brit. J. Clin. Pharmac.

Primary Examiner—Ronald W. Griffin

[57] ABSTRACT

Compositions and a general method are described to shorten the duration of common colds by administration of medicaments to and into the oral tissues, rather than to the nose, or by injection or by oral administration. Compositions for oral absorption by a human contain medicinal agents including antiviral agents, antirhinoviral agents, interferon, interferon inducers, T-cell lymphocyte mitogens and other agents desirable or theoretically useful in shortening the duration of common colds. All compositions include medicaments contained in a consumable, sweet pharmaceutical carrier, prepared in the form of a pleasant tasting lozenge, powder, liquid or chewable composition. All compositions are for delivery of medicinal agent to the oral and oral pharyngeal mucosa of a human with said composition being absent the normal offensive aftertaste of medicinal agent, and being intended for use in shortening the duration of common colds. The application specifically claims the discovery of utility of the application of medicinal agents to the oral and oralpharyngeal mucous membranes rather than the nose or by ingestion as the preferred method of administration of medicaments to shorten the duration of the common cold.

5 Claims, No Drawings

U.S. PATENT DOCUMENTS

| | | | |
|---|---|---|---|
| 3,331,696 | 7/1967 | Rieckmann et al. | 424/464 |
| 3,598,122 | 8/1971 | Zaffaroni | 424/435 |
| 3,789,119 | 1/1974 | Fusari et al. | 514/772.7 |
| 3,911,099 | 10/1975 | DeFoney et al. | 424/435 |
| 3,972,995 | 8/1976 | Tsuk et al. | 424/435 |
| 4,024,520 | 5/1977 | Palm | 424/464 |
| 4,059,686 | 11/1977 | Tanaka et al. | 424/435 |
| 4,115,544 | 9/1978 | Shell | 514/772.7 |
| 4,382,924 | 5/1983 | Berling et al. | 514/974 |
| 4,474,753 | 10/1984 | Haslam et al. | 514/772.7 |
| 4,503,070 | 3/1985 | Eby | 514/494 |
| 4,551,329 | 11/1985 | Harris et al. | 424/439 |
| 4,572,832 | 2/1986 | Kigasawa et al. | 514/774 |
| 4,684,534 | 8/1987 | Valentine | 424/447 |
| 4,747,881 | 5/1988 | Shaw et al. | 514/774 |
| 4,764,364 | 8/1988 | Heller et al. | 514/772.7 |
| 4,764,378 | 8/1988 | Keith et al. | 424/464 |
| 4,843,098 | 6/1989 | Shaw et al. | 514/774 |
| 4,915,948 | 4/1990 | Gallopo et al. | 524/464 |
| 5,002,970 | 3/1991 | Eby | 424/974 |
| 5,024,997 | 6/1991 | Motola et al. | 514/974 |
| 5,059,416 | 10/1991 | Cherukuri et al. | 514/974 |
| 5,073,374 | 12/1991 | McCarty | 424/464 |

GENERAL METHOD OF SHORTENING THE DURATION OF COMMON COLDS BY APPLICATION OF MEDICAMENTS TO TISSUES OF ORAL CAVITY

This application is a continuation-in-part of applicant's copending applications U.S. Ser. No. PCT/US91/09487, filed Dec. 17, 1991 and U.S. Ser. No. 07/633,043 filed Dec. 24, 1990, now U.S. Pat. No. 5,095,035, which is a continuation-in-part application of U.S. Ser. No. 07/182,983, filed Apr. 18, 1988, now U.S. Pat. No. 5,002,970 and a continuation-in-part of application U.S. Ser. No. 07/102,750, filed Sep. 24, 1987 now U.S. Pat. No. 4,956,385, which is a continuation of application Ser. No. 06/667,097, filed Nov. 1, 1984, now abandoned, which is a continuation-in-part application of Ser. No. 06/378,479, filed May 14, 1982, now U.S. Pat. No. 4,503,070, issued Mar. 5, 1985, reissued on Nov. 27, 1990 as U.S. Pat. No. Re. 33,465, which is a continuation-in-part application of U.S. Ser. No. 06/288,750, filed Jul. 31, 1981, now abandoned which is a continuation-in-part application of U.S. Ser. No. 06/022,620, filed Jan. 5, 1981 now abandoned.

FIELD OF INVENTION

This invention relates to a general method for reducing the duration of common colds and reducing the severity of common cold symptoms by applying medicament to the oral cavity rather than by applying medicament to the nose, by injection or by oral ingestion.

More particularly, this invention relates to the application of medicaments including antiviral agents, antirhinoviral agents, interferon, interferon inducers, T-cell lymphocyte mitogens, decongestant, drying agents, astringents, antihistamines, antibradikinins and all other pharmaceutical agents suitable for shortening the duration of common colds, reducing the severity of symptoms or otherwise beneficially treating common colds. Such medicaments are combined with a pharmaceutically acceptable carrier including fructose, sugar and the like with other necessary ingredients such as extra sweeteners, flavors, stabilizers and lubricants. Such compositions, when applied to oral and oral pharyngeal membranes of a human, are palatable and without undesirable taste or aftertaste yet allow oral and oral pharyngeal absorption of those agents intended to shorten or otherwise beneficially modify the course of a common cold in a human.

GENERAL BACKGROUND

Common colds, acute viral infections of the nose usually caused by rhinoviruses, are the most common acute illness in the United States and account for about one-half of all lost school days and lost work days. They are a major public health problem. An estimated one billion colds occur in the United States each year. Thus there can be no question as to the need for an improved method of administering antiviral agents, antirhinoviral agents, interferon, interferon inducers, T-cell lymphocyte mitogens, decongestants, drying agents, astringents, antihistamines, antibradikinins, and all other pharmaceutical agents suitable for shortening the duration of common colds that aid in minimizing said public health problem. Until recently, treatment of the common cold involved use of symptomatic therapy or soluble and ionizable zinc compounds applied to the oral and oralpharyngeal mucosa. Said zinc treatment was the first oral treatment to be used to shorten the common cold. All previous therapy, except treatment with interferon in some very specialized instances, do not reduce the duration of common colds when applied to the nose, by injection, or by the oral route via swallowing medicament. For example, with or without treatment, half of all colds last 7 days and the average duration of common colds is about 10 days, as the half-life of untreated common colds is 7 days. Primary common cold symptoms are nasal drainage and nasal congestion. Secondary symptoms often accompanying primary cold symptoms include headache, fever, myalgia, sneezing, sore throat, scratchy throat, cough and hoarseness and occasionally bronchial-sinusitis symptoms.

RELATED ART

Detailed study of zinc compounds used to treat common colds has revealed much about the nature of the oral cavity in the treatment of the common cold. It was found that certain compounds of zinc were more effective in treating colds than other zinc compounds and zinc compositions while some others were not effective at all. The basic conclusion derived from these findings relates to the presentation and availability of positively charged zinc ions for rapid antirhinoviral, antihistamine-like, interferon inducing and T-cell mitogenic effects as zinc ion is widely reported as having all said properties in vitro. Results using positively charged zinc ion compositions to shorten the common cold are reported in:

G. A. Eby et al., (1984), "Reduction in Duration of Common Cold Symptoms by Zinc Gluconate Lozenges in a Double Blind Study", *Antimicrobial Agents and Chemotherapy*, 25:20–24.

W. Al-Nakib et al., (1987), "Prophylaxis and Treatment of Rhinovirus Colds with Zinc Gluconate Lozenges", *Journal of Antimicrobial Chemotherapy*, 20:893–901.

Sequestrants are chemicals that deactivate or stabilize metallic ions by chemically tying up positively charged metal ions through chemical reactions to form stable, neutrally or negatively charged complexes. However, desirability of strongly sequestering metal ions in all cases must be challenged in view of nature of some metal chelators relative to environments in which their use is intended. For example, use of zinc gluconate in lozenges and similar means has been described as a method for reducing duration of common cold symptoms (U.S. Pat. No. 4,503,070, Mar. 5, 1985 and its reissue U.S. Pat. No. Re. 33,465). In such usage, zinc ions are only weakly bound by the gluconate moiety. The first stability constant of zinc gluconate is log $K_1 = 1.70$. Thirty percent or more of zinc appears as positively charged zinc ions in acidic to neutral pHs with remainder being positively charged zinc gluconate. Such ions are available for those antiviral, antirhinoviral, interferon inducing, T-cell lymphocyte mitogenic, decongestant, astringents, antihistamine-like, and antibradikinin-like biochemical activities in oral and oral pharyngeal mucous membranes that result in a major reduction in duration of common cold symptoms, which starts on the first day of treatment. Although the exact nature of biochemical activities of zinc ions in reducing duration of common cold symptons remains to be determined, it is conclusive that zinc must be present as positively charged ions to produce the most rapid results perhaps via the antirhinoviral, antihistamine-like, and interferon inducing effects of zinc ions.

Various decongestants and antihistamines have been administered by use of lozenges, troches and other orally active means, with beneficial results in the treatment of common colds, but without reduction in the duration of common colds. There are many example of decongestants and antihistamines being administered to the oral mucosa including menthol and eucalyptol lozenges of many brands such as Halls ® Throat Lozenges, Chloraseptic ®  Lozenges, Sucrets ®, Vicks Throat Lozenges ®, all of which contain decongestants or antihistamines.

ERRORS IN THE ART OF MEANS OF ADMINISTRATION OF COMMON COLD MEDICAMENTS

Although zinc 2+ when applied to the oral tissues is effective in shortening common colds by several means, zinc ions from zinc gluconate when applied to the nasal tissues in the form of drops or sprays do not shorten the duration of common colds, but do provide some antihistamine-like and decongestant activity much like zinc borate, a commonly used nasal decongestant in the 1950s. Since zinc gluconate works in the oral cavity but not in the nose, this inventor believes and teaches that all suitable common cold medicaments such as antiviral agents, antirhinoviral agents, interferon, interferon inducers, T-cell lymphocyte mitogens, decongestant, drying agents, astringents, antihistamines, antibradikinins, and all other pharmaceutical agents suitable for treating common colds will have efficacy, or greater efficacy, when applied to the oral mucosa than when applied to the inside of the nose, injected or swallowed.

Generally, antiviral agents, antirhinoviral agents, interferon, interferon inducers, T-cell lymphocyte mitogens, astringents, antibradikinins, and all other pharmaceutical agents suitable for shortening common colds either do not produce good results or produce poor results when applied to the nasal tissues, injected or orally administered by swallowing.

Interferons have shown promise as a treatment against common colds when used intranasally, but cause side effects sometimes worse than the cold when used in doses sufficient to have chemotherapeutic value. Various studies suggest that interferon does not appear to be a suitable candidate for prevention or treatment of common colds.

Enviroxime (2-amino-1-(isopropyl sulphenyl)-6-benzimidazole phenyl ketone oxime), a nontoxic but strong and broad spectrum antirhinoviral agent against 83 out of 83 rhinovirus serotypes, was particularly disappointing as it failed to demonstrate efficacy after topical nasal administration to common cold suffers.

Dichloroflavan, a substituted flaven which is relatively water insoluble, very non-toxic antirhinoviral agent in vitro, given in sufficient doses to produce very high levels of it in the blood stream also failed to shorten the duration of common colds.

A highly nontoxic synthetic compound, 2{(1,5101-tetrahydro-3H-thiazolo[3,4b]isoquinolin-3-ylidene)amino}-4-thiazoleacetic acid (S), or 44 081 RP for short, demonstrated good antirhinoviral effects in vitro but had no significant effect on common colds.

Many other chemotherapeutic agents have been studied and demonstrated to have in vitro effects, but were either too toxic or inefficacious when used in vivo.

SUMMARY OF INVENTION

This invention is a new means to accelerate clinical improvement of patients using antirhinoviral agents, antiviral agents, interferon inducers, interferon, antibradikinins and other pharmaceutical agents to shorten the duration of common colds and to reduce the severity of symptoms.

Application of antiviral agents including antirhinoviral agents to the oral mucosa through the incorporation of said antiviral agents within a slow release lozenge or other similar oral means presents a new method of administration that has the potential to inject said medicament into the lymphatic system or otherwise to circulate into the nasal tissue and the locus of infection. Although the means by which zinc ion are transported into nasal tissues in the original demonstration of this technique is not known but is suspected to involve diffusion, osmosis and electrophroesis and drainage by the lymphatic system, it is suggested that the same means of transport would also apply to other antiviral agents.

All methods directed at reducing the duration of common colds through means of administering antiviral agents by swallowing, injection or by administration to the nose have proven unsatisfactory. Prior art generally teaches individual treatment of each symptom as needed to ameliorate such symptoms during their association with a common cold. The present invention teaches a method of treatment of the common cold to reduce the duration of all associated symptoms and reduction of viral titer.

This invention teaches that it is not the antiviral that has to date been a failure, rather it is the various means of administration of said antiviral agents that has failed. It is the nasal administration method that fails to allow efficacy, perhaps because natural circulation removes the agents from the locus of treatment more rapidly than the application rate by the dosages replaces them as was found by F. Y Aoki in "Distribution and Removal of Human Serum Albumin-Technetium 99m instilled intranasally," (1976) *British Journal of Clinical Pharmacology*, Volume 3 pages 869–878. Because it has been established in vitro that certain antiviral agents can inhibit replication of rhinoviruses, it has been generally thought that the frequent nasal administration of sufficiently concentrated antiviral agents should prevent continued viral replication and result in a reduction in the duration of common colds. Regardless of a theoretical justification and reasonableness for nasal application as a method of increasing antiviral agent concentration in that part of the nose believed to be infected by viruses, the columnar epithelium of the nasal mucosa, under the prior art methods of application, efficaciousness has been absent.

The current need: In as much as there is an important need to develop better utilization of common cold medicaments including antiviral, antirhinoviral agents, interferon, interferon inducers, T-cell mitogens, antibradikinins, and all other pharmaceutical agents suitable for shortening the duration of common colds and to develop lozenges and other similar oral means having a pleasant taste to introduce said agents into oral and oral pharyngeal mucous membranes primarily for treatment of common colds; and in as much as serious mistakes taken from the prior art in the way common cold medicaments have been administered; it is apparent that errors of the prior art must receive attention.

PRIMARY OBJECTIVE AND GENERAL DESCRIPTION OF INVENTION

Accordingly, it is a primary objective of this invention to disclose and claim an improved method of administering antiviral agents, antirhinoviral agents, interferon, interferon inducers, T-cell mitogens, antibradikinins, and all other pharmaceutical agents suitable for treating common colds by use of long lasting throat lozenges and similar oral means such as syrups, tablets, powders, sprays, liquids when intended to be held for a length of time so that medicament can be absorbed into oral and oral pharyngeal mucous membranes, and especially when said oral dissolution compositions are for use in shortening duration of common colds or their symptoms. These primary objectives and other objectives of this invention will be found apparent from the following general description and detailed examples.

This inventor discovered that application of zinc gluconate in the form of a throat lozenge applied to the oral mucosa each several wakeful hour in a repeated fashion shortens the duration of common colds by about 7 days. However, this inventor also found that administration of soluble and ionizable zinc gluconate to the nose failed to shorten common colds even when zinc gluconate was administered each 15 minutes.

From the observation that zinc (an antirhinoviral agent, an antihistamine, an astringent an interferon inducer, and a T-cell mitogen) shorten common colds when applied to the oral cavity, this inventor now teaches that the reason all antiviral agents, antirhinoviral agents, interferons, interferon inducers, T-cell mitogens, decongestants, drying agents, astringents, antihistamines, antibradikinins, protein precipitators and all other pharmaceutical agents suitable for shortening the duration of common colds or generally treating common colds fail, or produce limited results is because they are not applied to the lining of the mouth in a sustained and repeated fashion, rather they are applied to the more logical and more obvious treatment locus, the interior of the nose, or by a secondary route such as oral ingestion or by injection.

This inventor teaches that all antiviral agents, antirhinoviral agents, interferons, interferon inducers, T-cell mitogens, decongestants, drying agents, astringents, antihistamines, antibradikinins, protein precipitators and all other pharmaceutical agents suitable for treating common colds must be administered to the roof of the mouth, the interior cheeks of the mouth, the tongue, the oral mucosa, the oralpharyngeal mucosa and all other interior surfaces of the mouth and to the throat, about each 1 to 3 hours, in a suitable manner and in a sustained way for any common cold treatment to be effective.

This inventor now discloses and teaches as his invention the general method of administering antiviral agents, antirhinoviral agents, interferons, interferon inducers, T-cell mitogens, decongestants, drying agents, astringents, antihistamines, antibradikinins, and all other pharmaceutical agents suitable for treating common colds to the oral and pharyngeal mucosa in a sustained manner through use of long lasting lozenges or similar solid or liquid means over a sufficiently long enough period of time to bring about the reduction in duration of common colds or their symptoms. This inventor teaches that the efficacious use of antiviral agents, antirhinoviral agents, interferons, interferon inducers, T-cell mitogens, decongestant, drying agents, astringents, antihistamines, protein precipitators, antibradikinins, and all other pharmaceutical agents suitable for treating common colds is enhanced and optimized when said medicaments are not administered by swallowing the medicament, injected or by application to the nasal tissues directly, but are enhanced and optimized by indirect means applied through the oral and oralpharyngeal tissue route of administration by means of lozenges or similar solid or liquid means of administering said medicaments.

DETAILED DESCRIPTION OF THE INVENTION

This invention relates to medicinal compositions specifically containing medicaments such as antirhinoviral agents including interferon, interferon inducers, propanediamine, enviroxime, dichloroflaven, 44 081 RP; decongestants including pseudoephedrine hydrochloride, phenyleprine HCL, clemastine fumarate, dextromethorphan hydrobromide; astringents including tannic acid and other similar or dissimilar agents capable of precipitating proteins or inhibiting histamine release or stimulating T-cell lymphocytes; antihistamines such as pheniramine maleate, triprolidine hydrochloride; antibradykinins; T-cell lymphocyte mitogens such as PHA, Con-A, tannic acid, soluble but nonionizable zinc compounds and all other pharmaceutical agents suitable for treating common colds within a sweetened, consumable pharmaceutically acceptable carrier such as a lozenge or otherwise which is primarily intended to be used for slow absorption of said medicament into oral and oral pharyngeal tissues of a human.

Pharmaceutically acceptable carriers such as fructose, Mendell's Sugartab ®, Sweetrex ® or Emdex ®, sucrose, dextrose, maltose, lactose, sweetened water and the like, singularly or in combination, with following pharmaceutical necessities included singularly or in combination, as desired:

tablet binders for compressed tablets, lozenges and troches, flavor oils such as peppermint, methyl salicylate, menthol and eucalyptol, flavor oil stabilizers, including spray driers and cyclodextrins, coloring agents and dyes, glidants, including silica gel, tablet lubricants, including magnesium stearate and other medicinal agents and nutritional supplements either directly incorporated within compositions or chemically isolated through techniques including microencapsulated and inclusion within cyclodextrins.

Such compositions include solid forms such as tablets, troches, lozenges and powders; chewable forms such as chewing gums and soft candies; and liquid forms such as syrups, mouth washes and sprays. When said compositions are applied to oral and oral pharyngeal membranes of a human, they are palatable and without undesirable taste or unpleasant aftertaste.

Surprising and unexpected flavor characteristics: Most importantly, very surprisingly and totally unexpectedly, with all of the tested medicinal agents previously described when diluted with any sweet, consumable, pharmaceutically acceptable carriers such as sweetened water, fructose, sucrose, dextrose, sweetened starch, sweetened lactose or other sweet dilutants, and particularly when saccharin or acesulfame K are present, the resultant products can be very pleasant tasting. Addition of saccharin eliminates bitterness associated with bitter medicaments.

Favored compositions of fructose or sucrose with medicinal agents: It can now be revealed that preference is given to incorporation of the medicinal agents in a fructose and agglomerated sucrose based carrier over other sugars as they are the sweetest of the natural sugars and produce the best taste. Generally lozenges are made in a 2 to 6 gram size to allow a suitable dissolution rate for lozenges. Dissolution rate should be about 12 to 15 minutes in water bath testers at 37 C. degrees or about 30 minutes when dissolved in the mouth as a lozenge, although there is considerable variability (fifteen minutes to one hour and fifteen minutes), depending on the amount of saliva produced in response to the lozenges. Smaller and bigger lozenges from 0.1 up to 15 grams were made with some medicaments and all are anticipated by this invention. The majority of most lozenges, perhaps 50 to 99 percent, is pharmaceutical carrier.

COMPRESSED TABLET COMPOSITIONS: Lozenges, tablets and troches in this invention are essentially the same, but may differ in shape size and manufacturing technique. Since fructose is sweeter than sucrose, and other sugars, it is preferred for use in direct compression of lozenges. Fructose may be processed for direct compression of tablets, troches and lozenges by incorporation of a tablet binder such as PEG-8000, perhaps using fluid bed agglomeration techniques wherein PEG has been diluted with water. To make directly compressible lozenges, medicament to PEG-8000 processed fructose; or add medicament to crystalline fructose and commercially available, sweet, direct compression products such as Mendell's Sugartab®, Sweetrex®, or Emdex®. Add saccharin if desired, flavors as desired, glidants such as silica gel as needed, and lubricants such as magnesium stearate (about 0.5 to 1.0%) as needed. Mixture should be kept dry, preferably less than 0.5% water. Ingredients are mixed and directly compressed into lozenges, tablets or troches using conventional pharmaceutical mixing and tableting equipment. Store in air tight containers in a cool dark place. If sufficient saccharine is included, no flavors are needed for compositions to have sweet pleasant tastes and no offensive aftertaste.

Hard Candy Compositions: Hard candy lozenges made from sucrose and corn syrup or other melted hard candy bases may be used for incorporation of any medicament that is not heat sensitive.

Soft compositions: Medicinal agent in fructose or sucrose chewable compositions such as a soft candy, gum drop, liquid filled candies or chewing gum base may be prepared by adding medicinal agent and fructose or sucrose to said soft bases.

Liquid compositions: Medicinal agents with a sweet, consumable pharmaceutically acceptable carrier may be prepared in any liquid form such as syrups, mouth washes or sprays with water or other liquids for repeated delivery of concentrated medicinal agent to the oral and oral pharyngeal mucous membranes over a sustained period of time so as to permit a prolonged contact of medicinal agent in the mouth.

Super sweeteners: Various super sweeteners including saccharine, acesulfame K, aspartame, cyclamates, monoammoniated glycerrhizins, neohesperidin dihydrochalcone and other super sweeteners may be added as desired to sweeten compositions.

Flavors: Many flavorings can be added to impart their own flavor including but not restricted to anise, anethole, eucalyptol, wintergreen, licorice, clove, cinnamon, spearmint, cherry, lemon, orange, lime, menthol, peppermint and various combinations.

Examples of invented compositions: The following examples will serve to further illustrate, but not to limit, the present invention. As it is not possible to demonstrate all possible combinations and dosages, it is obvious that many variations can exist and that the following examples are representative of means of administering any of said medicinal agents, including all antivirals, all antirhinovirals, interferon, interferon inducers, T-cell mitogens, all antibradykinins, and all other agents that might have an effect on the duration of common colds. Data demonstrating the efficacy of each may be obtained in the future as time and funds permit.

Favored medicinal agent lozenges can be prepared by direct compression of ingredients.

To make a 5-gram fructose based lozenge containing medicinal agent mix standard dose of medicinal agent (example interferon 1 to 20 million IU on silica gel), saccharin, 50 mg magnesium stearate (lubricant) and sufficient directly compressible sucrose and fructose to make a five gram lozenge. Compress with tablet press using sufficient pressure to obtain desired dissolution rate. About 6.5 tons of pressure using a hand press on a properly prepared ⅜ inch diameter 5-gram lozenge results in a 12 to 15 minute dissolution rate in water bath testers. Such composition has a pleasant sweet taste and no unpleasant aftertaste.

To make a 5-gram sucrose based lozenge containing medicinal agent (example 0.1 to 300 mg tannic acid, preferably about 50 to 150 mg tannic acid as a T-cell lymphocyte mitogen), mix medicinal agent, 40 mg or as desired saccharin, peppermint flavor, magnesium stearate (lubricant) and sufficient sucrose (such as Mendell Sugartab®) to make a five gram lozenge. Compress with tablet press using sufficient pressure to obtain desired dissolution rate. Such composition, either in powder form or solid, has a pleasant taste.

To make a 5-gram sucrose based lozenge containing medicinal agent (dichloraflaven), mix medicinal agent, 40 mg or as desired saccharin, wintergreen flavor, magnesium stearate (lubricant) and sufficient sucrose (such as Mendell Sugartab®) to make a five gram lozenge. Compress with tablet press using sufficient pressure to obtain desired dissolution rate. Such composition, either in powder form or solid, has a pleasant taste.

To make a 5-gram sucrose based lozenge containing medicinal agent (propanediamine), mix medicinal agent, 40 mg or as desired saccharin, spearmint flavor, magnesium stearate (lubricant) and sufficient sucrose (such as Mendell Sugartab®) to make a five gram lozenge. Compress with tablet press using sufficient pressure to obtain desired dissolution rate. Such composition, either in powder form or solid, has a pleasant taste.

To make a 5-gram sucrose based lozenge containing medicinal agent (PHA as a T-cell lymphocyte mitogen), mix medicinal agent, 40 mg or as desired saccharin, cherry flavor, magnesium stearate (lubricant) and sufficient sucrose (such as Mendell Sugartab®) to make a five gram lozenge. Compress with tablet press using sufficient pressure to obtain desired dissolution rate. Such composition, either in powder form or solid, has a pleasant taste.

To make a 5-gram sucrose based lozenge containing medicinal agent (antibradykinins), mix medicinal agent, 40 mg or as desired saccharin, clove flavor, magnesium stearate (lubricant) and sufficient sucrose (such as Mendell Sugartab ® to make a five gram lozenge. Compress with tablet press using sufficient pressure to obtain desired dissolution rate. Such composition, either in powder form or solid, has a pleasant taste.

To make a 5-gram dextrose based lozenge containing medicinal agent (example enviroxime 0.25 mg), mix medicinal agent, cherry flavor, saccharine, 50 mg magnesium stearate and sufficient dextrose to make a five gram lozenge. Compress with tablet press using sufficient pressure to obtain desired dissolution rate. Such composition has a pleasant taste.

To make a 5-gram lactose based lozenge containing a medicinal agent (example 0.3 mg 44 081 RP), mix standard dose of medicinal agent, saccharine as desired, 75 mg magnesium stearate (lubricant) and sufficient directly compressible lactose to make a five gram lozenge. Compress with tablet press using sufficient pressure to obtain desired dissolution rate. Such composition has a pleasant taste.

To make a 5-gram maltose based lozenge containing a medicinal agent, mix standard dose of medicinal agent (example an interferon inducer), saccharine, 75 mg magnesium stearate (lubricant) and sufficient directly compressible PEG prepared maltose to make a five gram lozenge. Compress with tablet press using sufficient pressure to obtain dissolution rate. Such composition has a pleasant taste.

To make a 5-gram hard candy based lozenge containing a medicinal agent, liquify by heating a hard candy base (a mixture of sucrose and corn syrup for example), add medicinal agent such as propanediamine, flavor and super sweetener if desired, mix, cool and package. Regardless of the bitterness of the medicinal agent, addition of saccharin or asulfame K corrects the bitterness problem.

To make a syrup wherein each 7.5 milliliter dose contains a standard dose of medicinal agent (example 1 to 10 million IU interferon), add to 5 grams of deionized water, 2.5 grams of fructose or sucrose, standard dose of medicinal agent, saccharin if desired, and flavors as desired. Vary amount of water and fructose to make other liquids such as mouth washes, gargles, and sprays. Such composition has a pleasant taste.

To make a chewing gum add to 4 grams of chewing gum base, about 5 grams of fructose, and standard dosage of medicinal agent, saccharin if desired and flavors as desired. To make a soft candy, substitute soft candy for chewing gum base. Such compositions may be thermally, chemically and flavor stable having a pleasant taste and no unpleasant aftertaste depending upon other ingredients added.

COMMENTS AND OTHER EXAMPLES

Preferred medicinal agent composition: The preferred method of applying medicinal agents to the oral mucosa is with fructose and agglomerated sucrose based lozenges of a size that the dosage will be administered for at least 15 minutes and preferably 30 minutes. Five gram ⅝ inch diameter agglomerated sucrose/fructose based lozenges (50/50 ratio) provide adequate dissolution times when compressed at maximum pressures. All dosage forms should be repeated each several hours until all symptoms have been absent for 6 to 12 hours. All ingredients to be used in compositions within the present invention are consumable (meaning dissolvable, swallowable, suckable, chewable and so forth) and are believed safe for human consumption.

Importance of Invention: Flavorful slow release oral medicinal compositions are important in that zinc gluconate lozenges have been shown to shorten the duration of common colds in clinical trials. It is therefore now taught that all other medicinal agents capable of reducing the duration of common colds will be either effective, or more effective, if administered by route of the oral mucosa. Common colds require orally applied medicinal treatment about every one to three hours in order to shorten them. Highly palatable oral medicinal compositions are needed as encouragement for a person in need of such treatment to continue treatment until symptoms are eliminated. Above examples may well serve to demonstrate that palatable medicinal lozenges and other similar compositions without unpleasant taste and aftertaste are possible using a fructose, sucrose or other sweet diluent.

Release rates: As will be apparent from examples, the amount of medicinal agent which will be released into the oral and oral pharyngeal mucosa can be controlled by the amount of medicinal agent incorporated in compositions. As will be readily understood, if a larger composition with a larger or smaller ratio of fructose, sucrose or other base to medicinal agent is used, that such is anticipated. Also, as will be readily understood, other release rates of medicinal agent and tablet bases, hard molded candies, syrups, mouth washes, gargles, tablets, liquids, chewing gums, powders, sprays, and aerosols may be used and are anticipated to dispense medicinal agents into the oral tissues. Any means suitable for delivery of medicinal agent and a consumable, sweet pharmaceutically acceptable carrier to oral and oral pharyngeal mucous membranes to permit a pleasant prolonged contact of medicinal agent in the mouth may be used and is anticipated. Present invention provides pleasant new means of releasing medicinal agent in the oral cavity, in various amounts, and at various rates determined by the formulation and composition used in a manner that is a substantial improvement in flavor, thermal and chemical stability over plain or otherwise flavored medicinal agent compounds.

As will be apparent to one skilled in the art, variations can be made within the scope of the aforesaid description. Such variations being within the ability of one skilled in the art form a part of the present invention and are embraced by following claims.

I claim:

1. A composition for use within the oral cavity that shortens the duration of common colds in a human through oral and oral pharyngeal absorption of an antirhinoviral medicament selected from the group consisting of interferon, interferon inducers, propanediamine, enviroxime, dichloroflaven, and 2{(1,5101-tetrahydro-3H-thiazolo[3,4b]isoquinolin-3-ylidene)amino}-4-thiazoleacetic acid (S) which are dispersed either singularly or in combination in a sweet pharmaceutically acceptable carrier as a lozenge, troche, syrup or other similar oral composition, whereby said composition excludes sodium polyacrylate and has a pleasant taste and aftertaste, and the medicament is released in a slow sustained manner in the oral cavity to facilitate absorption of the medicament into the oral and oral pharyngeal membranes.

2. The composition of claim 1 wherein said composition is a lozenge containing a standard dose of medicament dispersed in about 0.1 to about 15 grams of said sweet pharmaceutically acceptable carrier.

3. The composition of claim 2 wherein said composition is a lozenge containing a standard dose of medicament dispersed in about 1 to about 7 grams of said sweet pharmaceutically acceptable carrier.

4. The composition of claim 1 wherein said sweet pharmaceutically acceptable carrier is selected from the group consisting of fructose, sucrose, dextrose, maltose, and lactose.

5. The method of shortening the duration of common colds in a human in need of treatment comprising often repeated administration of a composition which excludes sodium polyacrylate within the oral cavity, with said composition containing an antirhinoviral medicament selected from the group consisting of interferon, interferon inducers, propanediamine, enviroxime, dichloroflaven, and 2{(1,5101-tetrahydro-3H-thiazolo[3,4b]isoquinolin-3-ylidene)amino}-4-thiazoleacetic acid (S) whereby said composition is a pleasant tasting lozenge, troche, syrup or other similar oral composition that releases said medicament in a slow sustained manner in the oral cavity to facilitate absorption of the medicament into the oral and oral pharyngeal membranes.

* * * * *